(12) United States Patent  
Ponzi et al.

(10) Patent No.: US 8,079,982 B1
(45) Date of Patent: Dec. 20, 2011

(54) INJECTION CATHETER WITH NEEDLE ELECTRODE

(75) Inventors: Dean M. Ponzi, Glendora, CA (US); Asher Holzer, Haifa (IL); Shlomo Ben-Haim, Haifa (IL)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/711,648

(22) Filed: Nov. 13, 2000

Related U.S. Application Data

(63) Continuation-in-part of application No. 09/280,202, filed on Mar. 29, 1999, now Pat. No. 6,165,164.

(60) Provisional application No. 60/088,019, filed on Jun. 4, 1998, provisional application No. 60/088,984, filed on Jun. 11, 1998.

(51) Int. Cl.
*A61M 5/00* (2006.01)
*A61M 31/00* (2006.01)

(52) U.S. Cl. ............ 604/115; 604/117; 604/95.01

(58) Field of Classification Search ............ 604/523, 604/507, 508, 93.01, 95.01, 95.04, 117; 606/41, 606/42

See application file for complete search history.

(56) References Cited

U.S. PATENT DOCUMENTS

| 3,598,119 A | 8/1971 | White |
| 4,270,535 A | 6/1981 | Bogue et al. |
| 4,578,061 A | 3/1986 | Lemelson |
| 4,966,597 A * | 10/1990 | Cosman ............ 606/50 |

(Continued)

FOREIGN PATENT DOCUMENTS

JP 2-139649 11/1990

(Continued)

OTHER PUBLICATIONS

Goette, A., M.D. et al; "Transcatheter Subendocardial Infusion, A Novel Technique for Mapping and Ablation of Ventricular Myocardium", Circulation, vol. 94, No. 6, Sep. 1996, pp. 1449-1455.

(Continued)

*Primary Examiner* — Kevin C Sirmons
*Assistant Examiner* — Michael J Anderson
(74) *Attorney, Agent, or Firm* — Christie, Parker & Hale, LLP

(57) ABSTRACT

An injection catheter for infusing therapeutic and diagnostic agents into the heart is provided. The injection catheter comprises a catheter body comprising a flexible tubing having proximal and distal ends and at least one lumen therethrough. A tip section comprising a flexible tubing having proximal and distal ends is mounted at the distal end of the catheter body. A needle control handle is provided at the proximal end of the catheter body. An injection needle extends through the tip section, catheter body, and needle control handle and has a proximal end attached to the needle control handle and a distal end within the tip section. The injection needle is longitudinally slidable within the tip section so that its distal end can extend beyond the distal end of the tip section upon suitable manipulation of the needle control handle. The catheter further comprises an electrode lead wire having a first end electrically connected to the injection needle and a second end electrically connected to a suitable monitoring apparatus or to a source of ablation energy. The injection needle can thus be used for mapping or ablation in addition to introducing therapeutic and diagnostic agents into the heart.

39 Claims, 11 Drawing Sheets

U.S. PATENT DOCUMENTS

| | | | |
|---|---|---|---|
| 5,244,460 A | | 9/1993 | Unger et al. |
| 5,318,525 A | * | 6/1994 | West et al. ............... 604/95.04 |
| 5,354,279 A | | 10/1994 | Hofling |
| 5,370,675 A | * | 12/1994 | Edwards et al. ............. 607/101 |
| 5,383,923 A | | 1/1995 | Webster, Jr. |
| 5,403,311 A | * | 4/1995 | Abele et al. ..................... 606/49 |
| 5,419,777 A | | 5/1995 | Hofling |
| 5,431,168 A | | 7/1995 | Webster, Jr. |
| 5,431,649 A | | 7/1995 | Muller et al. ................... 606/41 |
| 5,435,805 A | * | 7/1995 | Edwards et al. ............... 604/22 |
| 5,464,395 A | | 11/1995 | Faxon et al. |
| 5,522,815 A | * | 6/1996 | Durgin et al. ................... 606/50 |
| 5,554,110 A | * | 9/1996 | Edwards et al. ............... 604/22 |
| 5,588,432 A | | 12/1996 | Crowley |
| 5,599,294 A | * | 2/1997 | Edwards et al. ............... 604/22 |
| 5,661,133 A | | 8/1997 | Leiden et al. |
| 5,725,524 A | | 3/1998 | Muller et al. ................... 606/41 |
| 5,741,320 A | | 4/1998 | Thornton et al. ............. 607/122 |
| 5,797,870 A | | 8/1998 | March et al. |
| 5,810,804 A | * | 9/1998 | Gough et al. ................... 606/41 |
| 5,827,278 A | | 10/1998 | Webster, Jr. |
| 5,833,715 A | | 11/1998 | Vachon et al. ................ 604/120 |
| 5,857,997 A | | 1/1999 | Cimino et al. .................. 604/95 |
| 5,876,340 A | | 3/1999 | Tu et al. ........................ 600/439 |
| 5,891,138 A | | 4/1999 | Tu et al. .......................... 606/41 |
| 5,906,613 A | | 5/1999 | Muller et al. ................... 606/41 |
| 5,921,982 A | * | 7/1999 | Lesh et al. ...................... 606/41 |
| 6,004,295 A | * | 12/1999 | Langer et al. ............ 604/164.01 |
| 6,123,699 A | | 9/2000 | Webster, Jr. |
| 6,171,277 B1 | | 1/2001 | Ponzi |
| 6,179,809 B1 | | 1/2001 | Khairkhahan et al. |
| 6,183,463 B1 | | 2/2001 | Webster, Jr. |
| 6,309,370 B1 | | 10/2001 | Haim et al. |
| 6,468,260 B1 | | 10/2002 | Bumbalough et al. |
| 6,623,474 B1 | | 9/2003 | Ponzi |

FOREIGN PATENT DOCUMENTS

| | | |
|---|---|---|
| JP | 04022370 | 1/1992 |
| JP | 8504613 T | 5/1996 |
| JP | 11239619 A | 9/1999 |
| WO | WO 00/35531 | 6/2000 |

OTHER PUBLICATIONS

Marshall, D. J. et al., "Biocompatibility of Cardiovascular Gene Delivery Catheters with Adenovirus Vectors: An Important Determinant of the Efficiency of Cardiovascular Gene Transfer", Molecular Therapy, vol. 1, No. 5, May 2000, Part 1 of 2 Parts, pp. 423-429.

* cited by examiner

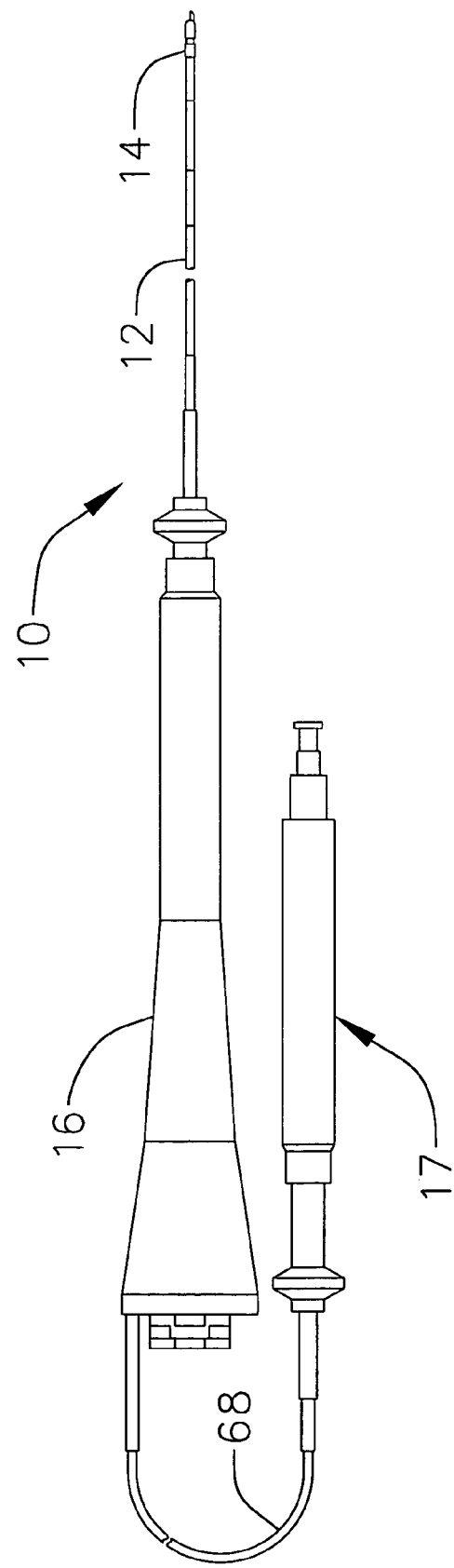

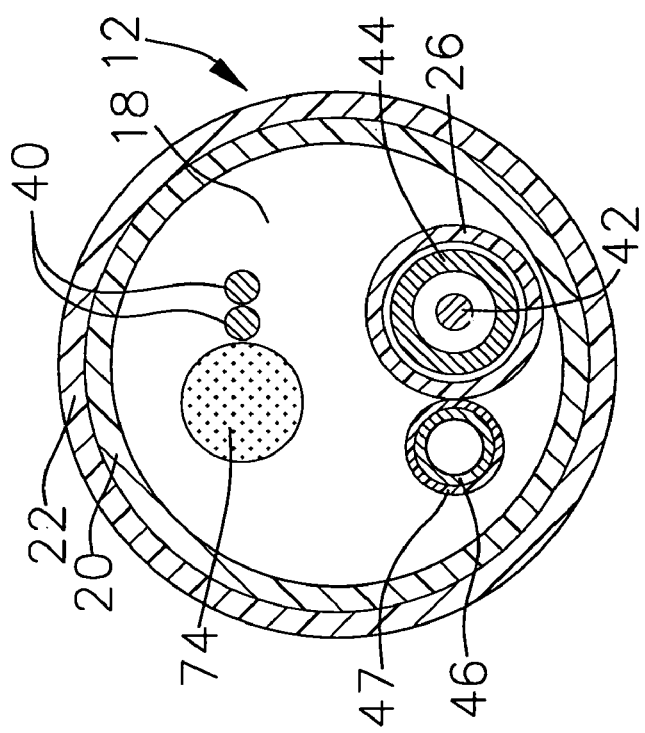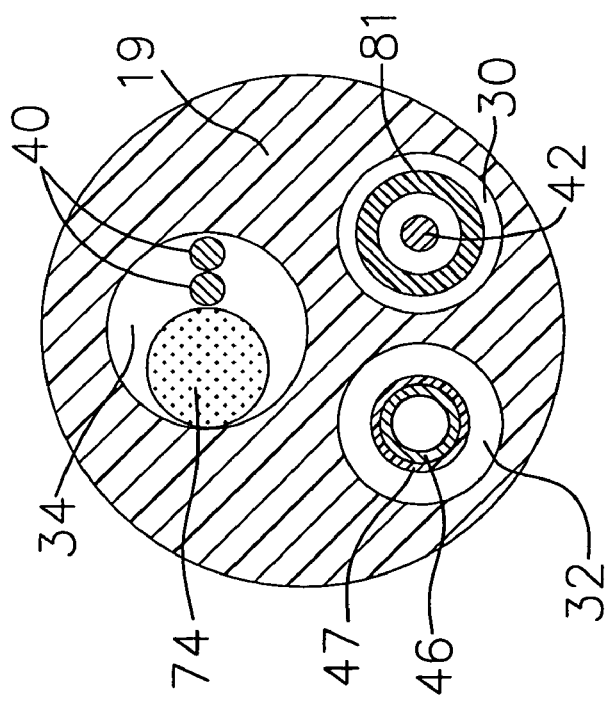

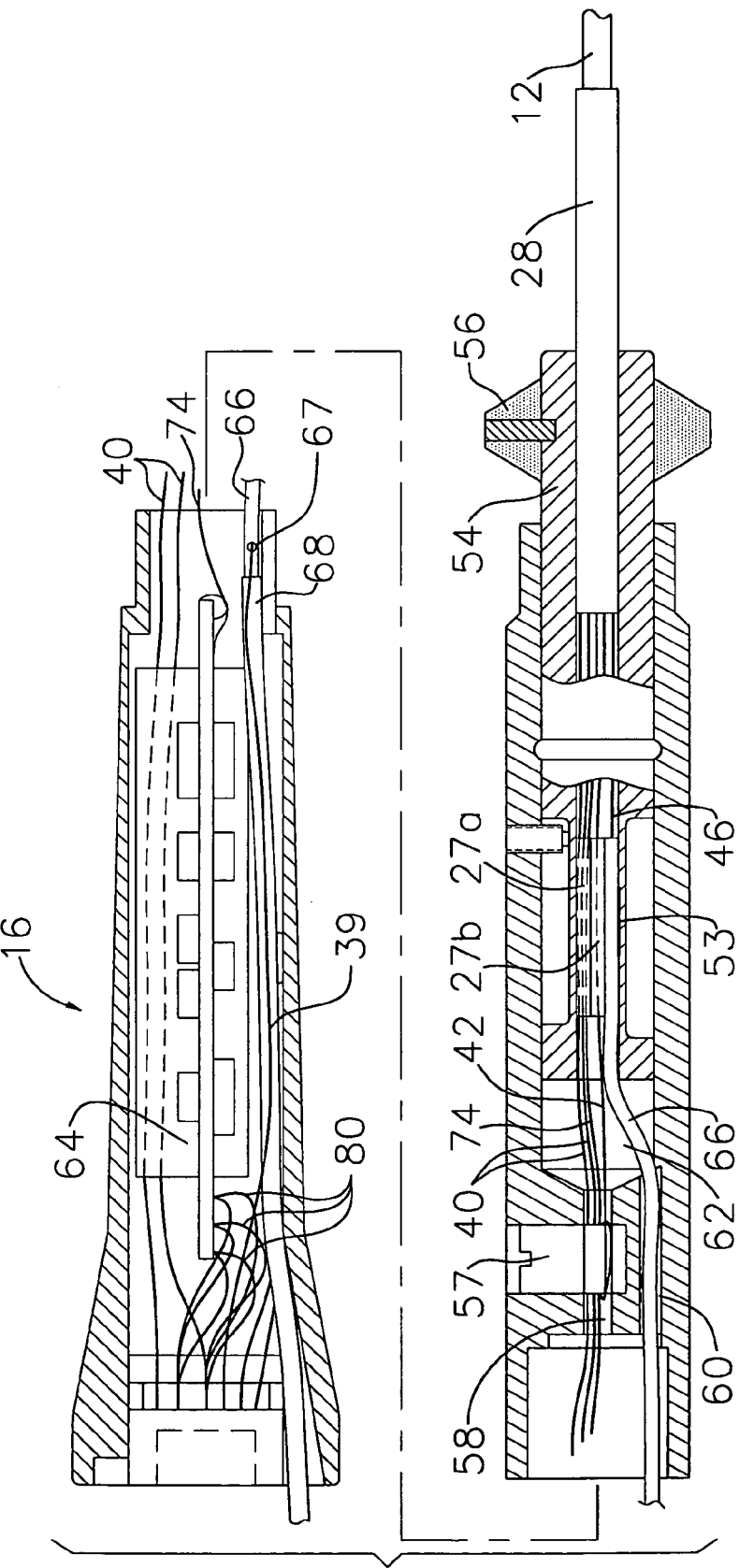

INJECTION CATHETER WITH NEEDLE ELECTRODE

CROSS-REFERENCE TO RELATED APPLICATION

This application is a continuation-in-part of U.S. patent application Ser. No. 09/280,202, filed Mar. 29, 1999 now U.S. Pat. No. 6,165,164, which claims the benefit of U.S. Provisional Patent Application Nos. 60/088,019, filed on Jun. 4, 1998, and 60/088,984, filed on Jun. 11, 1998, the entire disclosures of which are incorporated herein by reference.

FIELD OF THE INVENTION

This invention relates to a catheter for infusing therapeutic or diagnostic agents into the tissue of organs having an injection needle that also serves as an electrode for mapping and/or ablation.

BACKGROUND OF THE INVENTION

Targeted delivery of therapeutic or diagnostic agents, such as occurs in gene therapy, is very desirable but often presents a difficult challenge. A potential benefit of targeted delivery is that there is an increased efficiency obtained by the precise placement of the therapeutic or diagnostic agent. There are several problems to his procedure which must be overcome in order to obtain satisfactory results from such therapy, such as the problems of obtaining access to the delivery site, transporting the therapeutic or diagnostic agent to the desired site, injecting the agent at the proper depth within the organ tissue, steering the distal end of the catheter to a desired location within the organ prior to infusing the agent, and positioning the distal tip of the catheter at precisely the same location where prior measurements have indicated that the drug should be infused. It is also important to for a physician to be able to monitor the position of the infusion needle with respect to the wall of the organ. In the case of an organ, such as the heart, in which the walls are in constant motion, the activity of positioning and monitoring the position of the distal tip of the catheter, or infusion needle, becomes especially difficult.

U.S. Pat. No. 3,598,119 discloses a medical device for injecting drugs in which the injection needle is guided through an inner lumen of a catheter for insertion of the needle under skin tissue. A bladder at the distal end of the catheter may be inflated through another lumen for holding the point of the needle point in a fixed position beneath the skin.

U.S. Pat. No. 4,578,061 discloses a catheter for injecting a liquid into a vein, or artery, through an injection needle which is longitudinally movable beyond the distal end of the catheter. A dual chamber system is utilized within the catheter tip to provide for movement of a plunger to extend the injection needle and also to allow for a plunger to be used to apply a predetermined dose of medication through the injection needle.

U.S. Pat. No. 4,578,061 discloses an injection catheter having a longitudinal movable needle which may be moved through a lumen in order to extend out of the side wall of the catheter for injecting a liquid into a blood vessel. The needle is normally retracted into the device so that the needle will not penetrate tissue as the device is moved through a body duct. Thereafter, the needle is moved out of the side of the catheter into a vessel wall in order to infuse a liquid into the wall of a vessel.

U.S. Pat. No. 5,244,460 is directed toward a method for improving blood flow to the heart. More particularly this patent is directed toward a medical procedure for improving the growth of cardiac blood vessels by inserting a catheter into a coronary artery and injecting into the heart a blood vessel growth promoting peptide through an injection port of the catheter.

U.S. Pat. No. 5,419,777 is directed toward a catheter for injection of a fluid into body cavities such as coronary vessels and arteries. This patent, as is the case with the '061 patent, illustrates the use of an injection needle which protrudes laterally through the side walls of the distal tip of the catheter. In the case of drug injections to be made into coronary vessels and arteries, it is very desirable to have the needles extend out of the side walls of the catheter and at an acute angle to the walls of the vessel in order to penetrate the walls of the vessel for injection of the agent.

U.S. Pat. No. 5,431,168, assigned to the same assignee as the present patent application, is directed toward a steerable catheter which includes a puller wire for controlling the distal end of the catheter from a control handle which is mounted on the proximal end of the catheter.

Copending U.S. patent application Ser. No. 09/019,453, entitled "Intracardiac Drug Delivery," assigned to an affiliated company of the assignee of this application, discloses an injection catheter system for infusing a diagnostic or therapeutic agent into the wall of an organ which includes an electromagnetic sensor disposed within the distal tip of the catheter for providing very precise location information for the distal tip of the catheter. The subject matter of this copending patent application is incorporated by reference into the subject patent application.

SUMMARY OF THE INVENTION

This present invention is directed to a catheter for infusing therapeutic or diagnostic agents into the tissue of organs wherein the injection needle can also be used for mapping and ablation. In one embodiment, the injection catheter comprises a catheter body comprising a flexible tubing having proximal and distal ends and at least one lumen therethrough. A tip section comprising a flexible tubing having proximal and distal ends is mounted at the distal end of the catheter body. It is understood that the tip section and catheter body can be two separate components fixedly attached together or a single integral tubing wherein the tip section is the distal end of the tubing on which is mounted, for example, the tip electrode and ring electrodes.

A needle control handle is provided at the proximal end of the catheter body. An injection needle extends through the tip section, catheter body, and needle control handle and has a proximal end attached to the needle control handle and a distal end within the tip section. The injection needle is longitudinally slidable within the tip section so that its distal end can extend beyond the distal end of the tip section upon suitable manipulation of the needle control handle. An electrode lead wire is electrically connected to the injection needle and to a suitable monitoring apparatus or to a source of ablation energy.

In another embodiment, the invention is directed to a method for introducing a therapeutic or diagnostic agent into heart tissue of a patient. The method comprises introducing the distal end of a catheter as described above into the patient's heart. The injection needle is extended beyond the distal end of the tip section, and it is determined whether the injection needle has penetrated the heart tissue, preferably by measuring the impedance across the distal end of the injection needle. If the injection needle has penetrated the tissue, the therapeutic or diagnostic agent is injected into the heart tissue with the injection needle. Otherwise, the physician can reposition the distal end of the catheter and again attempt to penetrate the heart tissue.

In another embodiment, the invention is directed to a catheter comprising a catheter body, tip section and needle control handle as described above. An injection needle extends through the tip section, catheter body, and needle control handle and has a proximal end attached to the needle control handle and a distal end within the tip section. The injection needle is longitudinally slidable within the tip section so that its distal end can extend beyond the distal end of the tip section upon suitable manipulation of the needle control handle. An electrode is mounted on the injection needle near the distal end of the injection needle and electrically isolated from the injection needle. An electrode lead wire is electrically connected to the electrode and to a suitable monitoring apparatus or to a source of ablation energy.

In another embodiment, the invention is directed to a method for introducing a therapeutic or diagnostic agent into heart tissue of a patient. The method comprises introducing the distal end of a catheter as described in the preceding paragraph into the patient's heart. The injection needle is extended beyond the distal end of the tip section, and it is determined whether the injection needle has penetrated the heart tissue, preferably by measuring the impedance across the electrode mounted on the injection needle. If the injection needle has penetrated the tissue, the therapeutic or diagnostic agent is injected into the heart tissue with the injection needle. Otherwise, the physician can reposition the distal end of the catheter and again attempt to penetrate the heart tissue.

DESCRIPTION OF THE DRAWINGS

These and other features and advantages of the present invention will be better understood by reference to the following detailed description when considered in conjunction with the accompanying drawings wherein:

FIG. 1 is a side plan view of one embodiment of the catheter of the present invention.

FIG. 6 is a transverse cross-sectional view of the tip section of FIG. 3 along line 6-6 showing an embodiment having three lumens.

FIG. 7 is a transverse cross-sectional view of the catheter body along line 7-7.

FIG. 8 is a side cross-sectional view of the catheter handle according to the invention.

DETAILED DESCRIPTION

Figure 2A:
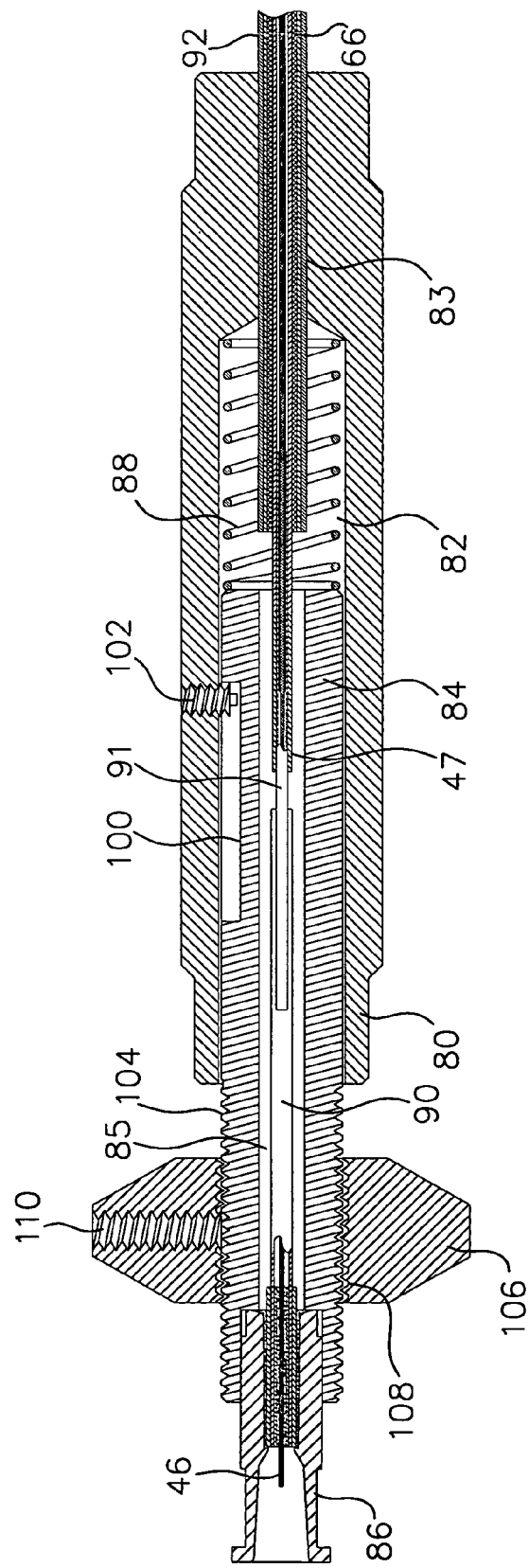
FIG. 2a is a side cross-sectional view of the needle control handle where the needle is in a retracted position.

In a preferred embodiment of the invention, there is provided a catheter for use for injection of a therapeutic or diagnostic agent into the heart. As shown in FIG. 1, catheter 10 comprises an elongated catheter body 12 having proximal and distal ends, a tip section 14 at the distal end of the catheter body, a deflection control handle 16 at the proximal end of the catheter body, and a needle control handle 17 proximal the catheter body.

Figure 5:
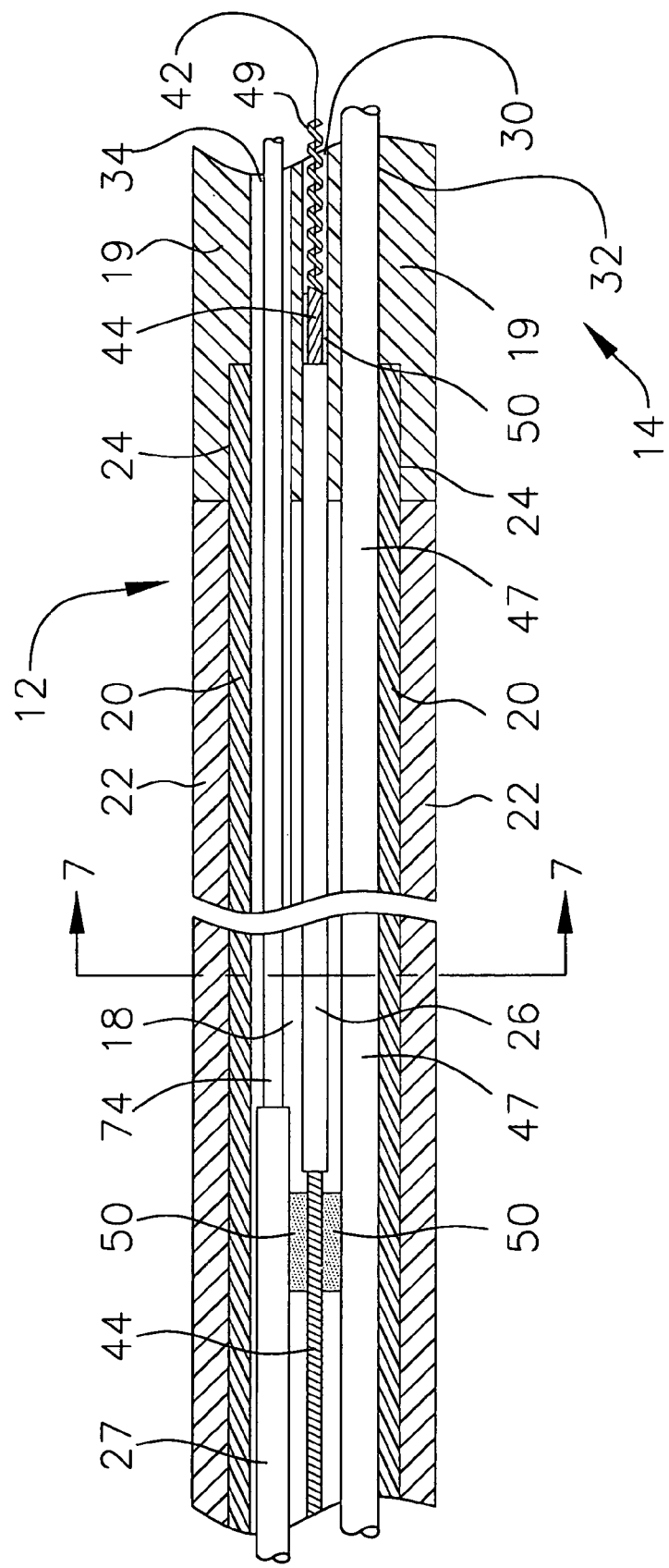
FIG. 5 is a side cross sectional view of the catheter body, including the junction between the catheter body and the section.

With reference to FIGS. 5 and 7, the catheter body 12 comprises a single, central or axial lumen 18. The catheter body 12 is flexible, i.e., bendable, but substantially non-compressible along its length. The catheter body 12 may be of any suitable construction and made of any suitable material. A presently preferred construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section 14 of the catheter will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is presently preferred because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used. If desired, the stiffening tube 20 can be eliminated.

Figure 3A:
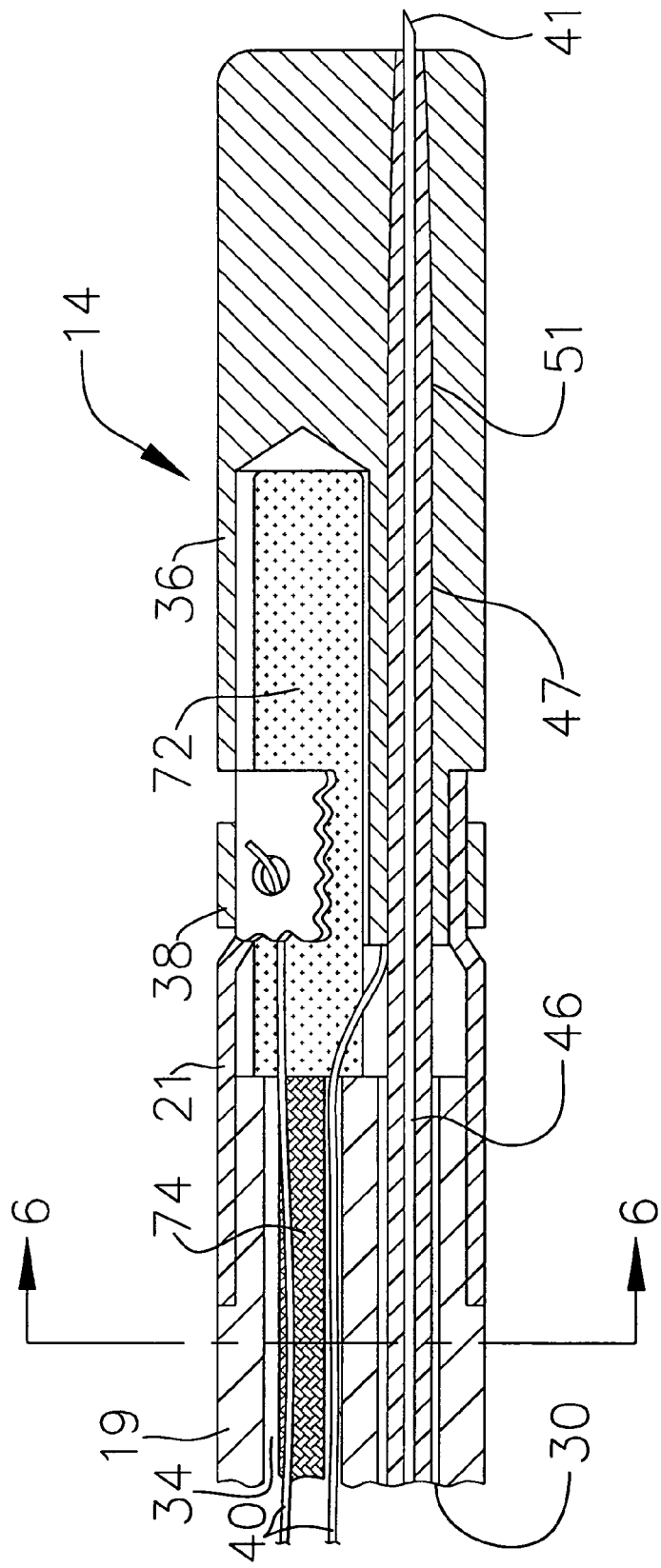
FIG. 3A is a side cross-sectional view of a tip section according to the invention having three lumens, showing the position of the electromagnetic mapping sensor and the injection needle.
Figure 4:
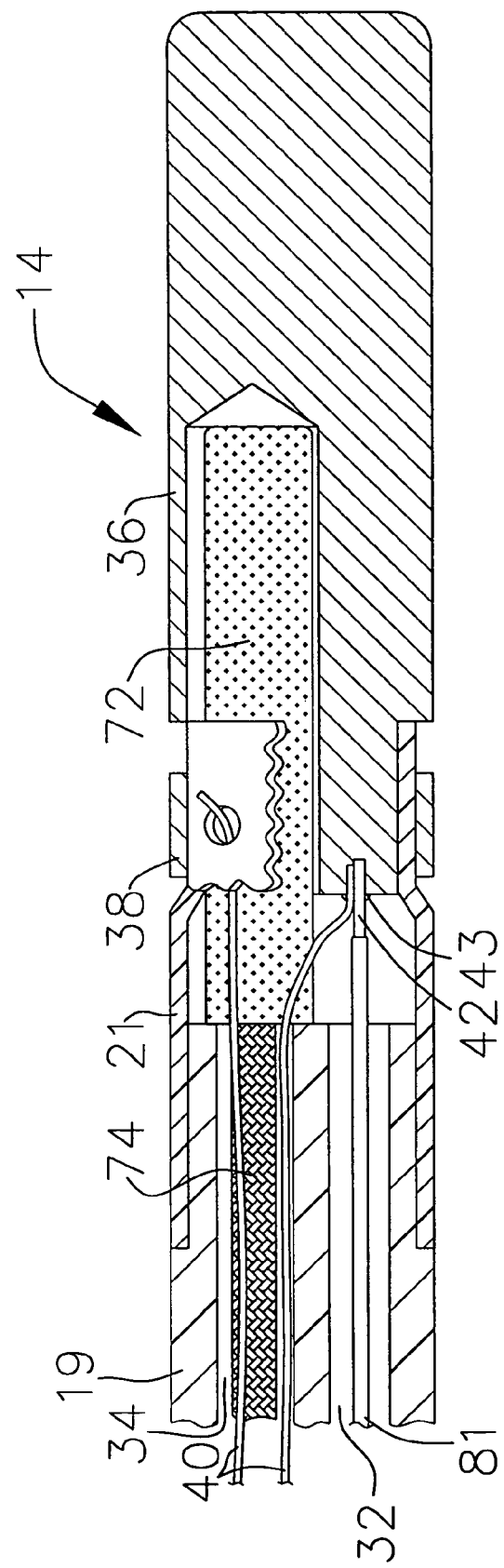
FIG. 4 is a side cross-sectional view of the tip section of FIG. 3A showing the position of the electromagnetic mapping sensor and the puller wire.

As shown in FIGS. 3A, 4 and 6, the tip section 14 comprises a short section of tubing 19 having three lumens 30, 32 and 34. The tubing 19 is made of a suitable non-toxic material that is preferably more flexible than the catheter body 12. A presently preferred material for the tubing 19 is braided polyurethane, i.e., polyurethane with an embedded mesh of braided stainless steel or the like. The outer diameter of the tip section 14, like that of the catheter body 12, is preferably no greater than about 8 French. The size of the lumens is not critical. In a particularly preferred embodiment, the tip section has an outer diameter of about 7 French (0.092 inch) and the first lumen 30 and second lumen 32 are generally about the same size, having a diameter of about 0.022 inch, with the third lumen 34 having a slightly larger diameter of about 0.036 inch.

A preferred means for attaching the catheter body 12 to the tip section 14 is illustrated in FIG. 5. The proximal end of the tip section 14 comprises an inner counter bore 24 that receives the outer surface of the polyimide stiffener 20. The tip section 14 and catheter body 12 are attached by glue or the like.

The stiffening tube 20 is held in place relative to the outer wall 22 at the proximal end of the catheter body 12. In preferred construction of the catheter body 12, a force is applied to the proximal end of the stiffening tube 20 that causes the distal end of the stiffening tube to firmly push against the counter bore 24. While under compression, a first glue joint is made between the stiffening tube 20 and the outer wall 22 by a fast drying glue, e.g. Super Glue®. Thereafter a second glue joint is formed between the proximal ends of the stiffening tube 20 and outer wall 22 using a slower drying but stronger glue, e.g., polyurethane. Any other suitable method of attaching the catheter body 12 to the tip section 14 can be used.

Extending through the single lumen 18 of the catheter body 12 are lead wires 40, an injection needle 46, a sensor cable 74, and a compression coil 44 through which a puller wire 42 extends. A single lumen 18 catheter body is preferred over a multi-lumen body because it has been found that the single lumen 18 body permits better tip control when rotating the catheter 10. The single lumen 18 permits the lead wires 40, the injection needle 46, the sensor cable 74, and the puller wire 42 surrounded by the compression coil 44 to float freely within the catheter body. If such wires and cables were restricted within multiple lumens, they tend to build up energy when the handle 16 is rotated, resulting in the catheter body 12 having a tendency to rotate back if, for example, the handle is released, or if bent around a curve, to flip over, either for which are undesirable performance characteristics.

With reference to FIGS. 3A and 4, mounted at the distal end of the tip section 14 is a tip electrode 36. Preferably the tip electrode 36 has a diameter about the same as the outer diameter of the tubing 19. The tip electrode 36 is connected to the tubing 19 by means of a plastic housing 21, preferably made of polyetheretherketone (PEEK). The proximal end of the tip electrode 36 is notched circumferentially and fits inside the distal end of the plastic housing 21 and is bonded to the housing 21 by polyurethane glue or the like. The proximal end of the plastic housing 21 is bonded with polyurethane glue or the like to the distal end of the tubing 19 of the tip section 14. Alternatively, the tip electrode 36 can be mounted directly to the distal end of the flexible tubing 19 of the tip section 14, with the housing 21 eliminated.

Mounted on the distal end of the plastic housing 21 is a ring electrode 38. The ring electrode 38 is slid over the plastic housing 21 and fixed in place by glue or the like. Alternatively, if the plastic housing 21 is eliminated, the ring electrode can be positioned over the flexible tubing 19 of the tip section 14. If desired, additional ring electrodes may be used and can be positioned over the plastic housing 21 or over the flexible tubing 19 of the tip section 14.

The tip electrode 36 and ring electrode 38 are each connected to a separate lead wire 40. The lead wires 40 extend through the third lumen 34 of tip section 14, the catheter body 12, and the control handle 16, and terminate at their proximal end in an input jack (not shown) that may be plugged into an appropriate monitoring system for measuring and displaying electrical activity (not shown) and/or a source of RF energy (not shown). If desired, the portion of the lead wires 40 extending through the catheter body 12, control handle 16 and proximal end of the tip section 14 may be enclosed or bundled within a protective tube or sheath (not shown).

The lead wires 40 are attached to the tip electrode 36 and ring electrode 38 by any conventional technique. Connection of lead wire 40 to the tip electrode 36 is preferably accomplished by weld 43, as shown in FIG. 4.

A puller wire 42 is provided for deflection of the tip section 14. The puller wire 42 is anchored at its proximal end to the control handle 16 and anchored at its distal end in the tip section 14, as discussed in more detail below. The puller wire 42 is made of any suitable metal, such as stainless steel or Nitinol, and is preferably coated with Teflon® or the like. The coating imparts lubricity to the puller wire 42. The puller wire 42 preferably has a diameter ranging from about 0.006 to about 0.010 inches.

As discussed above, a compression coil 44 is provided in surrounding relation to a portion of the puller wire 42. The compression coil 44 extends from the proximal end of the catheter body 12 to the proximal end of the tip section 14. The compression coil 44 is made of any suitable metal, preferably stainless steel. The compression coil 44 is tightly wound on itself to provide flexibility, i.e., bending, but to resist compression. The inner diameter of the compression coil 44 is preferably slightly larger than the diameter of the puller wire 42. For example, when the puller wire 42 has a diameter of about 0.007 inches, the compression coil 44 preferably has an inner diameter of about 0.008 inches. The Teflon® coating on the puller wire 42 allows it to slide freely within the compression coil 44. Along most of its length, the outer surface of the compression coil 44 is covered by a flexible, non-conductive sheath 26 to prevent contact between the compression coil 44 and any of the lead wires 40, injection needle 46 or sensor cable 74. A non-conductive sheath 26 made of polyimide tubing is presently preferred.

In the depicted embodiment, the compression coil 44 is anchored at its proximal end to the proximal end of the stiffening tube 20 in the catheter body 12 by glue to form a glue joint 50 and at its distal end to the tip section 14 in the second lumen 32, also forming a glue joint 50. If a stiffening tube 20 is not used, the proximal end of the compression coil 44 can be glued directly to the outer wall 22 of the catheter body 12. The glue may be applied by means of a syringe or the like through a hole made between the outer surface of the catheter body 12 and the single lumen. Alternatively, the distal end of the compression coil 44 can be anchored in the distal end of the catheter body 12, for example, by gluing the compression coil to the stiffening tube 20 or the outer wall 22, if a stiffening tube is not used.

The puller wire 42 extends out of the distal end of the compression coil 44 and into the second lumen 32 of the tip section 14. The distal end of the puller wire 42 is anchored to the tip electrode 36 or to the side of the tip section 14 by any suitable method known in the art. Examples of suitable methods for anchoring the puller wire 42 in the tip section 14 are described in U.S. Pat. Nos. 5,383,923 and 5,827,278, the disclosures of which are incorporated herein by reference. With reference to FIGS. 4 and 5, within the tip section 14, and distal to the glue joint 50, the turns of the compression coil 44 are expanded 49 longitudinally. The expanded turns 49 are both bendable and compressible and preferably extend for a length of about 0.5 inch. The puller wire 42 extends through the expanded turns 49 then into a plastic, preferably Teflon®, sheath 81, which prevents the puller 42 from cutting into the wall of the tip section 14 when the tip section is deflected. If desired, the expanded turns 49 can be eliminated.

An extendable and retractable injection needle 46 is provided for injection of drugs and therapeutic and diagnostic agents into the heart tissue. The injection needle 46 extends from the needle control handle 17 through the catheter body 12, through the first lumen 30 of the tip section 14 and through a passage 51 in the tip electrode 36. As illustrated in FIG. 3A, the injection needle 46 is preferably formed with a beveled edge 41 at the distal tip of the needle. The needle 46 is coaxially mounted within a protective tube 47, preferably made of polyimide, which serves to prevent the needle from buckling and also serves to electrically insulate the needle from the tip electrode 36. The protective tube 47 additionally serves to provide a fluid-tight seal surrounding the injection needle 46 to prevent body fluids from entering the distal end of the catheter. Preferably the protective tube 47 is provided along the entire length of the injection needle 46, although it can cover only the distal portion of the injection needle if desired.

FIG. 3A depicts the injection needle 46 extending beyond the distal end of the tip electrode 36, as it would be positioned in order to infuse diagnostic or therapeutic fluid into the heart tissue. The catheter is designed to permit the distal end of the injection needle 46 to be withdrawn into the tip electrode 36 during the period of time that the catheter is inserted through the vasculature of the body and also during the period of time in which the catheter is removed from the body to avoid injury. Alternatively, the tip section 14 can be provided without a tip electrode 36, in which case the distal end of the injection needle 46 could be retracted into the first lumen 30 of the tip section 14. In either embodiment, the injection needle 46 is extendable and retractable beyond the distal end of the catheter. If desired, the catheter can include a needle stop mechanism for limiting the distance that the needle extends beyond the distal end of the tip section 14. Such a mechanism is described in copending U.S. patent application Ser. No. 09/563,769, entitled "Injection Catheter with Needle Stop" to Dean Ponzi, the entire disclosure of which is incorporated herein by reference.

The injection needle 46 is made from one or more straight pieces of small diameter tubing having an outer diameter that allows the tubing to fit within the catheter. Preferably the injection needle 46 has an inner diameter ranging from about 0.007 inch to about 0.011 inch, and an outer diameter ranging from about 0.012 inch to about 0.016 inch. Preferably the injection needle 46 has a total length ranging from about 65 to about 85 inches, more preferably about 75 inches, although the length can vary as desired depending on the length of the catheter in which it is used and the application for which it is to be used.

In one embodiment, the injection needle 46 is formed of Nitinol or other conductive material. Alternatively, a portion of the needle is formed of plastic with the distal portion of the needle being formed of a conductive metal, such as Nitinol. The needle, whether all metal or part metal and part plastic, preferably has straight position memory so that when it is bent to a small radius, its natural tendency is to spring back to the straight position. This property is particularly important for the distal region of the injection needle (i.e., the portion of the needle within the tip section 14), because when the tip section is deflected, the needle will deflect with the tip section. When the tip section is then straightened from its deflected position, the memory of the distal region of the needle pushes the tip section back towards the straight position to the same axis as the catheter body. If desired, at least a portion of the tubing, such as the portion that forms the distal region of the needle, is provided with a lubricious coating, such as Teflon® or silicone, preferably having a thickness ranging from about 0.0003 inch to about 0.002 inch. In another alternative embodiment, a biocompatible lubricant, such as mineral oil is injected around the needle once assembled.

If desired, the distal end of the injection needle 46 is provide with one or more fluid openings (not shown) along its length. The fluid openings can be of any suitable shape, such as round, oval, or rectangular. The fluid openings can be provided only on one side of the needle 46, or about the circumference of the needle. The fluid openings enhance the ability of the drug or other agent passing through the needle to weep into the injection site and be more evenly distributed, allowing for better absorption of the agent by the heart tissue.

A needle electrode lead wire 39 is electrically connected to the injection needle 46 to permit the injection needle to also function as an electrode. In one embodiment, the injection needle 46 comprises metal along its entire length, and the needle electrode lead wire 39 is attached near the proximal end of the injection needle within the deflection control handle 16, as described in more detail below.

Figure 3B:
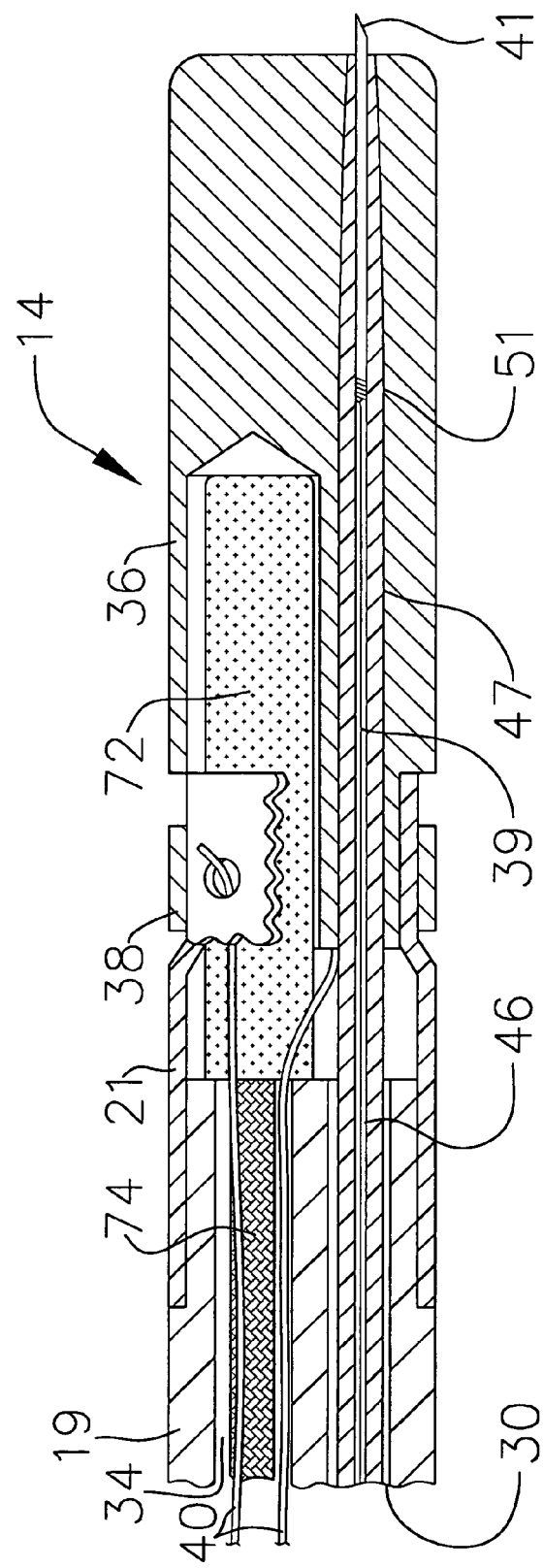
FIG. 3B is a side cross-sectional view of a tip section according to the invention showing a lead wire attached to the distal end of the injection needle.

In an alternative embodiment, as shown in FIG. 3B, the needle electrode lead wire 39 is electrically connected near the distal end of the injection needle 46 within the tip section 14. In this embodiment, the needle electrode lead wire 39 extends within the protective tube 47 along with the injection needle 46, and the distal end of the needle electrode lead wire is soldered, welded or otherwise electrically attached to the injection needle within the protective tube. In this embodiment, it is only necessary that the distal end of the injection needle 46, i.e., the end to which the needle electrode lead wire 39 is attached, be made of metal, and the remainder of the injection needle can be made of metal or plastic, as desired.

Preferably in this embodiment the needle electrode lead wire 39 comprises a pair of wires, a first wire of a high conductivity material (e.g., copper) and a second wire of a high strength material different from the first material (e.g., constantan) non-conductively bonded to the first wire. This pair of wires acts as a thermocouple in addition to an electrode lead wire. More details on such an arrangement are disclosed in U.S. Pat. No. 5,893,885, the disclosure of which is incorporated herein by reference. If desired, the portion of the injection needle 46 to which the needle electrode lead wire 39 is attached can be covered with a thin coating of Teflon or the like (not shown) to enhance the ability of the injection needle to slide within the protective tube 47 and to prevent the needle electrode lead wire from getting stuck or caught on the protective tube as the injection needle is being slid in and out of the tip section 14.

The injection needle 46 can be used to infuse therapeutic agents, diagnostic agents and the like. Particularly preferred agents include angiogenesis activators, angiogenesis inhibitors, and antiarrhythmic drugs. Examples of angiogenesis activators include vascular endothelial growth factor, vascular endothelial growth factor receptor, neuropilin-1, angiopoietins, such as Ang1, tyrosine kinases (Tie), such as Tie2, transforming growth factor-$\beta 1$, transforming growth factor-$\beta$ receptors, endoglin, chemokines, hepatocyte growth factor, monocyte chemoattractant protein-1 integrins, such as $\alpha_v\beta_3$, $\alpha_v\beta_5$, $\alpha_5\beta_1$, VE-cahedrin, platelet-endothelial cell-adhesion molecule, ephrins, plasminogen activators, matrix metalloproteinases, and cyclo-oxygenase-2. Examples of angiogenesis inhibitors include vascular endothelial growth factor receptor-1, neuropilin-1, angiopoietins, such as Ang2, angiostatin and related plasminogen kringles, endostatin (collagen XVIII fragment), vasostatin, calreticulin, platelet factor-4, matrix metalloproteinase inhibitors, prothrombin kringle-2, antithrombin III fragment, maspin, canstatin, proliferin-related protein, and restin. Examples of antiarrhythmic drugs include sodium channel blockers, potassium channel blockers, membrane-stabilizing agents, and $\alpha$-adrenoceptor blockers, $\beta$-adrenoceptor blockers and calcium channel blockers.

In use, the injection needle 46 can function as a mapping electrode and/or as an ablation electrode. For example, the injection needle 46 can be used to map the electrical activity of the heart, alone or in combination with the tip electrode 36 and/or ring electrodes 38, prior to injection of a therapeutic or diagnostic agent into the heart tissue. Using this method, the physician can more precisely position the injection needle at a desired location. The invention is also contemplated for epicardial applications.

Alternatively, the injection needle 46 can be used to ablate heart tissue before, during or after injection of the therapeutic or diagnostic agent, as desired. Ablation often enhances the effectiveness of a therapeutic agent. Specifically, creating an injury that causes an inflammation response, which results in having white blood cells coming to injury site and fighting the inflammation, makes the target site susceptible to an agent.

Additionally, the injection needle 46 can be used to determine the extent of needle penetration in the heart tissue. For this methodology, it is preferred that the needle electrode lead wire 39 be attached to the proximal end of the injection needle 46. During a procedure, the physician monitors the impedance of the injection needle 46 relative to the tip electrode 36 (or a ring electrode 38, if a tip electrode is not used). If the distal end of the injection needle 46 is within the heart tissue, the difference in impedance will be relatively high (e.g., around 500 to 600Ω). Accordingly, the physician can then proceed to inject the therapeutic or diagnostic agent. In contrast, if the distal end of the injection needle 46 for some reason has not penetrated the heart tissue, but is only in contact with blood, the difference in impedance will be relatively low (e.g., around 100 to 150Ω). This information indicates to the physician that he or she should reattempt to penetrate the heart tissue with the needle before injecting the agent.

Figure 3C:
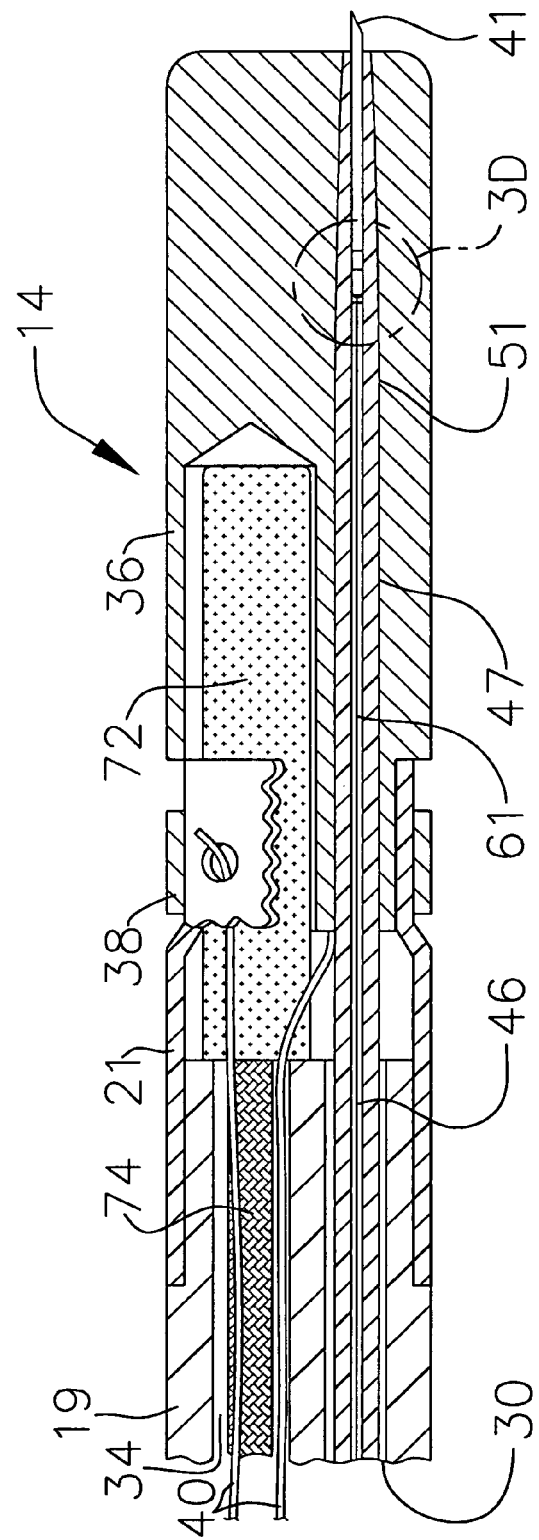
FIG. 3C is a side cross-sectional view of a tip section according to the invention showing an injection needle with a penetration-monitoring electrode mounted thereon.
Figure 3D:
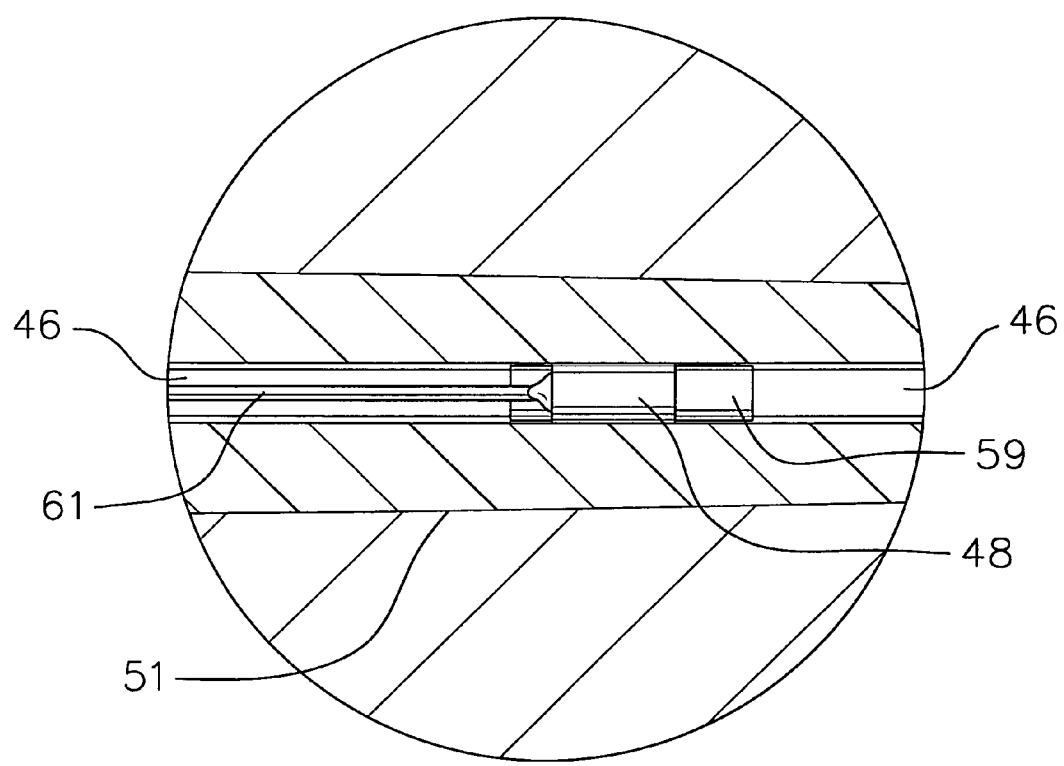
FIG. 3D is a close-up view of the penetration-monitoring electrode of FIG. 3C.

In another alternative embodiment, as shown in FIGS. 3C and 3D, a penetration-monitoring electrode 48 is mounted on the injection needle 46 for monitoring whether and to what extent the injection needle has penetrated the tissue. In the depicted embodiment, the penetration-monitoring electrode 48 is electrically isolated from the injection needle 46 by a thin non-conductive (preferably Teflon) covering 59 on the needle. The penetration-monitoring electrode 48 can be mounted by any other suitable non-conductive method, such as with polyurethane glue. A lead wire 61 is electrically connected to the penetration-monitoring electrode 48 by any suitable means, such as weld, solder, or the like. The penetration-monitoring electrode 48 is positioned at a position along the length of the injection needle 46 that generally corresponds to the desired depth that the needle penetrate the heart tissue. In this embodiment, the injection needle 46 may optionally also act as a separate electrode, i.e., have an electrode lead wire 39 electrically connected thereto.

In use, once the physician believes he or she has penetrated the tissue with the injection needle 46, he monitors the impedance of the penetration-monitoring electrode 48 relative to the tip electrode 36 (or a ring electrode 38). If the penetration-monitoring electrode 48 is in contact with the heart tissue, the difference in impedance will be relatively high, and if the penetration-monitoring electrode is not in contact with the tissue, but only in contact with blood, the difference in impedance will be relatively low. Similar to the method described above, this information indicates to the physician whether the injection needle has penetrated the heart tissue at the desired depth.

Additionally, a location sensor, preferably an electromagnetic location sensor 72, is contained within the distal end of the tip section 14. The electromagnetic sensor 72 is connected to the electromagnetic sensor cable 74, which extends through the third lumen 34 of the tip section 14 through the catheter body 12, and into the deflection control handle 16. The electromagnetic sensor cable 74 comprises multiple wires encased within a plastic sheath. In the deflection control handle 16, the wires of the sensor cable 74 are connected to a circuit board 64. The circuit board 64 amplifies the signal received from the electromagnetic sensor and transmits it to a computer in a form understandable by the computer. Also, because the catheter is designed for single use only, the circuit board contains an EPROM chip which shuts down the circuit board after the catheter has been used. This prevents the catheter, or at least the electromagnetic sensor, from being used twice. Suitable electromagnetic sensors for use in connection with the present invention are described, for example, in U.S. Pat. No. 4,391,199 and U.S. patent application Ser. No. 09/160,063, entitled "Miniaturized Position Sensor," the disclosures of which are incorporated herein by reference. A preferred electromagnetic mapping sensor 72 is manufactured by Biosense Webster, Inc. and marketed under the trade designation NOGA. To use the electromagnetic sensor 72, the patient is placed in a magnetic field generated, for example, by situating under the patient a pad containing coils for generating a magnetic field. A reference electromagnetic sensor is fixed relative to the patient, e.g., taped to the patient's back, and the injection catheter containing a second electromagnetic sensor is advanced into the patient's heart. Each sensor comprises three small coils which in the magnetic field generate weak electrical signals indicative of their position in the magnetic field. Signals generated by both the fixed reference sensor and the second sensor in the heart are amplified and transmitted to a computer which analyzes the signals and then displays the signals on a monitor. By this method, the precise location of the sensor in the catheter relative to the reference sensor can be ascertained and visually displayed. The sensor can also detect displacement of the catheter that is caused by contraction of the heart muscle.

Using this technology, the physician can visually map a heart chamber. This mapping is done by advancing the catheter tip into a heart chamber until contact is made with the heart wall. This position is recorded and saved. The catheter tip is then moved to another position in contact with the heart wall and again the position is recorded and saved.

The electromagnetic mapping sensor 72 can be used alone or, more preferably, in combination with the needle electrode 46, tip electrode 36 and/or ring electrode 38. By combining the electromagnetic sensor 72 and one or more of the electrodes 46, 36 and/or 38, a physician can simultaneously map the contours or shape of the heart chamber, the electrical activity of the heart, and the extent of displacement of the catheter and hence identify the presence and location of the ischemic tissue. Specifically, the electromagnetic mapping sensor 72 is used to monitor the precise location of the tip electrode in the heart and the extent of catheter displacement. The needle electrode 46, tip electrode 36 and ring electrode 38 can be used to monitor the strength of the electrical signals at that location. Healthy heart tissue is identified by strong electrical signals in combination with strong displacement. Dead or diseased heart tissue is identified by weak electrical signals in combination with dysfunctional displacement, i.e., displacement in a direction opposite that of healthy tissue. Ischemic, or hibernating or stunned, heart tissue is identified by strong electrical signals in combination with impaired displacement. Hence, the combination of the electromagnetic mapping sensor 72 and needle, tip and/or ring electrodes 46, 36 and 38 is used as a diagnostic catheter to determine whether and where to infuse a drug into the wall of the heart. Once the presence and location of ischemic tissue has been identified, the tip section 14 of the catheter can be deflected so that the injection needle 46 is generally normal, i.e., at a right angle, to the ischemic tissue. The injection needle 46 may then be extended out of the distal end of the tip electrode 36 (if not already extended for mapping purposes) and into the wall of the heart.

It is understood that, while it is preferred to include both electrophysiology electrodes and an electromagnetic sensor in the catheter tip, it is not necessary to include both. For example, an injection catheter having an electromagnetic sensor but no electrophysiology electrodes may be used in combination with a separate mapping catheter system. A preferred mapping system includes a catheter comprising multiple electrodes and an electromagnetic sensor, such as the NOGA-STAR catheter marketed by Biosense Webster, Inc., and means for monitoring and displaying the signals received from the electrodes and electromagnetic sensor, such as the Biosense-NOGA system, also marketed by Biosense Webster, Inc.

The electrode lead wires 40 and electromagnetic sensor cable 74 must be allowed some longitudinal movement within the catheter body so that they do not break when the tip section 14 is deflected. To provide for such lengthwise movement, there is provided a tunnel through the glue joint 50, which fixes the proximal end of the compression coil 44 inside the catheter body 12. The tunnel is formed by a transfer tube 27, preferably made of a short segment of polyimide tubing. Preferably the transfer tube 27 is approximately 60 mm long and has an outer diameter of about 0.021 inch and an inner diameter of about 0.019 inch.

Longitudinal movement of the puller wire 42 relative to the catheter body 12, which results in deflection of the tip section 14, is accomplished by suitable manipulation of the deflection control handle 16. As shown in FIG. 8, the deflection control handle 16 comprises a handle housing 52 and a piston 54 having an axial passage 55 and a thumb control 56. The proximal end of the catheter body 12 is connected to the piston 54 by means of a shrink sleeve 28.

The injection needle 46 within the protective tube 47, the puller wire 42, the lead wires 40 and the electromagnetic sensor cable 74 extend through the axial passage 55 of the piston 54. The puller wire 42 is anchored to an anchor pin 57 located proximal to the piston 54. The lead wires 40 and electromagnetic sensor cable 74 extend through a first tunnel 58 in the handle housing 52, located near a side of the deflection control handle 16. The electromagnetic sensor cable 74 connects to the circuit board 64 in the proximal end of the deflection control handle 16. Wires 80 connect the circuit board 64 to a computer and imaging monitor (not shown).

The injection needle 46 and protective tube 47 extend through a guide tube 66, preferably made of polyurethane, and are afforded longitudinal movement therein. The guide tube 66 is anchored to the piston 54, preferably by a glue joint 53. This design affords the injection needle 46 and protective tube 47 longitudinal movement within the deflection control handle 16 so that the needle does not break when the piston 54 is adjusted to manipulate the catheter body 12 relative to the handle housing 52 and the puller wire 42. Within the piston 54, the electromagnetic sensor cable 74 and lead wires 40 are situated within a first transfer tube 27a, and the puller wire 42 is situated within a second transfer tube 27b to allow longitudinal movement of the wires and cable near the glue joint 53.

The injection needle 46, protective tube 47 and guide tube 66 extend through a second tunnel 60 in the handle housing 52 situated near the side of the control handle 16 opposite the anchor pin 57. To avoid undesirable bending of the injection needle 46, a space 62 is provided in the handle housing 52 between the proximal end of the piston 54 and the distal end of the second tunnel 60. Preferably the space 62 has a length of at least about 0.50 inch and more preferably about from about 0.60 inch to about 0.90 inch.

In the proximal end of the deflection control handle 16, the injection needle 46, protective tube 47 and polyurethane guide tube 66 extend through a second larger plastic guide tube 68, preferably made of Teflon®, which affords the guide tube 66, injection needle 46, and protective tube 47 longitudinal slidable movement. The second guide tube 68 is anchored to the inside of the handle housing 52 by glue or the like and extends proximally beyond the control handle 16. The second guide tube 68 protects the injection needle 46 both from contact with the circuit board 64 and from any sharp bends as the guide tube 66, needle 46, and protective tube 47 emerge from the deflection control handle 16.

In the depicted embodiment, the needle electrode lead wire 39 is electrically connected to the injection needle 46 within the deflection control handle 16. Specifically, a hole 67 is provided in the guide tube 66 and protective tube 47. The needle electrode lead wire 39 passes through the hole 67 and is attached to the injection needle 46 by weld, solder or the like within the guide tube 66 and protective tube 47. Alternatively, for the embodiment depicted in FIG. 3B, where the needle electrode lead wire 39 is connected to the distal end of the injection needle 46, the needle electrode lead wire passes through the hole 67 and extends along the length of the injection needle 46 like within the guide tube 66 and protective tube 47.

Figure 2B:
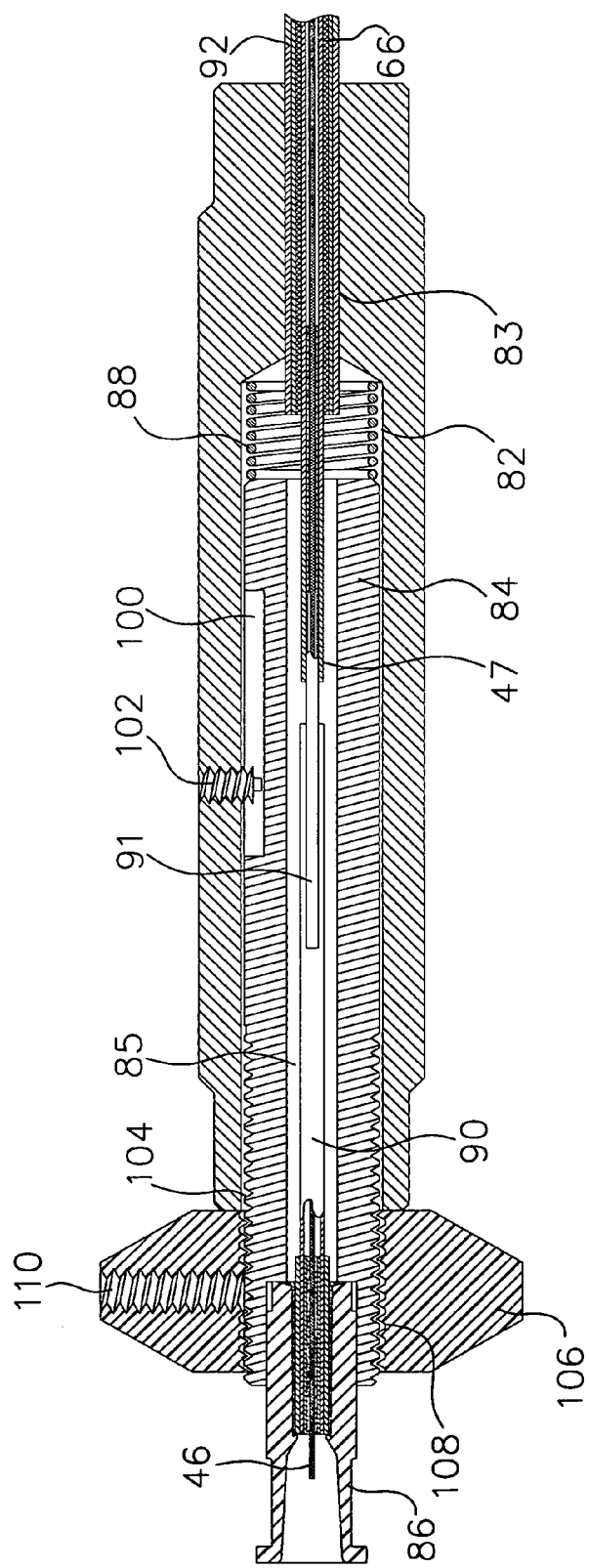
FIG. 2b is a side cross-sectional view of the needle control handle where the needle is in an extended position.

Extension and retraction of the injection needle 46 out the distal end of the tip electrode 36 is accomplished by the needle control handle 17. As illustrated in FIGS. 2a and 2b, the needle control handle 17 comprises a generally cylindrical outer body 80 having proximal and distal ends; a piston chamber 82 extending a part of the way therethrough, and a needle passage 83 extending a part of the way therethrough. The piston chamber 82 extends from the proximal end of the needle control handle part way into the body 80, but does not extend out the distal end of the body. The needle passage 83, which has a diameter less than that of the piston chamber 82, extends from the proximal end of the piston chamber to the proximal end of the outer body 80.

A piston 84, having proximal and distal ends, is slidably mounted within the piston chamber 82. The piston 84 has an axial passage 85 through which the injection needle 46 extends, as described in more detail below. A Luer connector 86 is mounted in the distal end of the outer body 80. A compression spring 88 is mounted within the piston chamber 82 between the distal end of the piston 84 and the outer body 80.

The proximal end of the injection needle 46 is mounted to the Luer connector 86 by means of a first rigid tube 90, preferably made of stainless steel, which has a proximal end fitted into the Luer connector. This arrangement fixedly attaches the injection needle 46 to the piston 84 so that it moves longitudinally with the piston. The first rigid tube 90 is also fixedly attached to the piston 84 and moves longitudinally with the piston. The injection needle 46 and first rigid tube 90 extend through the axial passage 85 of the piston 84. Within the axial passage 85, a second rigid tube 91, preferably made of stainless steel, has a proximal end mounted coaxially within the distal end of the first rigid tube 90. The proximal end of the second rigid tube 91 is mounted within the protective tube 47, which has its proximal end inside the axial passage 85, and the distal end of the second rigid tube is attached, directly or indirectly, to the outer body 80. The guide tube 66, through which the protective tube 47 and injection needle 46 extend, as discussed above, is fixedly attached to the outer body 80 by means of a shrink sleeve 92, as is generally known in the art.

In use, force is applied to the piston 84 to cause distal movement of the piston relative to the outer body 80, which compresses the compression spring 88. This movement causes the injection needle 46 to correspondingly move distally relative to the outer body, guide tube 66, protective tube 47 and catheter body 12, so that the distal end of the injection needle extends outside the distal end of the tip electrode 36. Upon distal movement of the piston 84, the first rigid tube 91 moves distally over the second rigid tube 91 to prevent the injection needle 46 from buckling within the axial passage 85. When the force is removed from the piston 54, the compression spring 88 pushes the piston 84 proximally to its original position, thus causing the distal end of the injection needle 46 to retract back into the tip electrode 36.

The piston 84 further comprises a longitudinal slot 100 extending along a portion of its outer edge. A set screw 102 extends through a hole in the outer body 80 and into the longitudinal slot 100. This design limits the distance that the piston 84 can be slid proximally out of the piston chamber 82, and, if desired, the distance that the piston can be slid distally to extend the injection needle 46. When the distal end of the injection needle 46 is in the retracted position, preferably the set screw 102 is at or near the distal end of the longitudinal slot 100.

The proximal end of the piston 84 has a threaded outer surface 104. A circular thumb control 106 is mounted on the proximal end of the piston 84. The thumb control 106 has a threaded inner surface 108 that interacts with the threaded outer surface 104 of the piston 84. The thumb control 106 acts as a stop, limiting the distance that the piston 84 can be pushed into the piston chamber 82, and thus the distance that the injection needle 46 can be extended out the distal end of the catheter. The threaded surfaces of the thumb control 106 and piston 84 allow the thumb control to be moved closer or farther from the proximal end of the outer body 80 so that the extension distance of the injection needle can be controlled by the physician. A tension screw 110 is provided in the thumb control 106 to control the tension between the thumb control and piston 84. As would be recognized by one skilled in the art, the thumb control 106 can be replaced by any other mechanism that can act as a stop for limiting the distance that the piston 84 extends into the piston chamber 82, and it is not necessary, although it is preferred, that the stop be adjustable relative to the piston.

In another preferred embodiment constructed in accordance with the present invention, two or more puller wires (not shown) are provided to enhance the ability to manipulate the tip section. In such an embodiment, a second puller wire and a surrounding second compression coil extend through the catheter body and into separate off-axis lumens in the tip section. The lumens of the tip section receiving the puller wires may be in adjacent quadrants. The first puller wire is preferably anchored proximal to the anchor location of the second puller wire. The second puller wire may be anchored to the tip electrode or may be anchored to the wall of the tip section adjacent the distal end of tip section.

The distance between the distal end of the compression coils and the anchor sites of each puller wire in the tip section determines the curvature of the tip section 14 in the direction of the puller wires. For example, an arrangement wherein the two puller wires are anchored at different distances from the distal ends of the compression coils allows a long reach curve in a first plane and a short reach curve in a plane 90° from the first, i.e., a first curve in one plane generally along the axis of the tip section before it is deflected and a second curve distal to the first curve in a plane transverse, and preferably normal to the first plane. The high torque characteristic of the catheter tip section 12 reduces the tendency for the deflection in one direction to deform the deflection in the other direction. Suitable deflection control handles for use with such a catheter are described in U.S. Pat. No. 6,123,699, entitled "Omni-Directional Steerable Catheter", and U.S. patent application Ser. No. 09/130,359, filed Aug. 7, 1998, entitled "Bi-Directional Control Handle for Steerable Catheter", Ser. No. 09/143,426, filed Aug. 28, 1998, entitled "Bidirectional Steerable Catheter with Bidirectional Control Handle", and Ser. No. 09/546,310, filed Apr. 10, 2000, entitled "Single Gear Drive Bidirectional Control Handle for Steerable Catheter", the disclosures of which are incorporated herein by reference.

As an alternative to the above described embodiment, two puller wires may extend into diametrically opposed off-axis lumens in the tip section. In such an embodiment, each of the puller wires may be anchored at the same location along the length of the tip section, in which case the curvatures of the tip section in opposing directions are the same and the tip section can be made to deflect in either direction without rotation of the catheter body.

The preceding description has been presented with reference to presently preferred embodiments of the invention. Workers skilled in the art and technology to which this invention pertains will appreciate that alterations and changes in the described structure may be practiced without meaningful departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. An injection catheter comprising:
a catheter body comprising a flexible tubing having proximal and distal ends and at least one lumen therethrough;
a tip section having a longitudinal axis and comprising a flexible tubing having proximal and distal ends, wherein the proximal end of the tip section is mounted at the distal end of the catheter body;
a needle control handle at the proximal end of the catheter body;
an injection needle extending through the tip section, catheter body, and needle control handle and having a proximal end attached to the needle control handle and a distal end within the tip section, wherein the injection needle is longitudinally slidable within the tip section so that upon suitable manipulation of the needle control handle the distal end of the injection needle can extend distally beyond the distal end of the tip section in a direction along the longitudinal axis of the tip section;
an electrode lead wire having a first end electrically connected to the injection needle and a second end electrically connected to a suitable monitoring apparatus or to a source of ablation energy; and
a penetration monitoring electrode fixedly mounted on the injection needle and electrically insulated from the injection needle.

2. An injection catheter according to claim 1, wherein the first end of the electrode lead wire is connected near the proximal end of the injection needle.

3. An injection catheter according to claim 1, wherein the first end of the electrode lead wire is connected near the distal end of the injection needle.

4. An injection catheter according to claim 3, wherein the electrode lead wire comprises a pair of wires including a copper wire and a constantan wire that can act as a thermocouple.

5. An injection catheter according to claim 1, further comprising a protective tube in surrounding relation to at least a portion of the injection needle.

6. An injection catheter according to claim 5, wherein the protective tube surrounds the injection needle along substantially the entire length of the needle.

7. An injection catheter according to claim 1, further comprising at least one additional electrode mounted on the tip section.

8. An injection catheter according to claim 1, further comprising a tip electrode mounted on the distal end of the tip section.

9. An injection catheter comprising:
a catheter body comprising a flexible tubing having proximal and distal ends and at least one lumen therethrough;
a tip section having a longitudinal axis and comprising a flexible tubing having proximal and distal ends, wherein the proximal end of the tip section is mounted at the distal end of the catheter body, the distal end having a distal face;
a needle control handle at the proximal end of the catheter body;
an injection needle extending through the tip section, catheter body, and needle control handle and having a proximal end attached to the needle control handle and a distal end within the tip section, wherein the injection needle is longitudinally slidable within the tip section so that upon suitable manipulation of the control handle the distal end of the injection needle can extend distally out the distal face of the tip section in a direction along the longitudinal axis of the tip section;
a penetration monitoring electrode fixedly mounted on the injection needle near the distal end of the injection needle and electrically isolated from the injection needle; and
an electrode lead wire having a first end electrically connected to the electrode and a second end electrically connected to a suitable monitoring apparatus or to a source of ablation energy.

10. An injection catheter according to claim 9, wherein the electrode is in the form of a ring mounted in surrounding relation to the injection needle.

11. An injection catheter according to claim 9, further comprising an electrode lead wire having a first end electrically connected to the injection needle and a second end electrically connected to a suitable monitoring apparatus or to a source of ablation energy.

12. A method for introducing a therapeutic or diagnostic agent into heart tissue of a patient comprising:
introducing the distal end of a catheter according to claim 1, into the patient's heart;
extending the injection needle distally beyond the distal end of the tip section;
determining whether the injection needle has penetrated the heart tissue by using the penetration monitoring electrode fixedly mounted on the injection needle; and
injecting a therapeutic or diagnostic agent into the heart tissue with the injection needle.

13. A method according to claim 12, wherein the determining step comprises measuring the impedance across the distal end of the injection needle.

14. A method according to claim 12, wherein the catheter further comprises at least one additional electrode at or near the distal end of the tip section.

15. A method according to claim 14, wherein the determining step comprises comparing the impedance across the distal end of the injection needle to the impedance across the additional electrode.

16. A method according to claim 12, wherein the therapeutic or diagnostic agent is selected from the group consisting of angiogenesis activators, angiogenesis inhibitors, and antiarrythmic drugs.

17. A method for introducing a therapeutic or diagnostic agent into heart tissue of a patient comprising:
introducing the distal end of a catheter according to claim 9 into the patient's heart;
extending the injection needle distally out the distal face of the tip section;
determining whether the injection needle has penetrated the heart tissue by using the penetration monitoring electrode fixedly mounted on the injection needle; and
injecting a therapeutic or diagnostic agent into the heart tissue with the injection needle.

18. A method according to claim 17, wherein the determining step comprises measuring the impedance across the electrode mounted on the injection needle.

19. A method according to claim 17, wherein the catheter further comprises at least one additional electrode at or near the distal end of the tip section.

20. A method according to claim 19, wherein the determining step comprises comparing the impedance across the electrode mounted on the injection needle to the impedance across the additional electrode.

21. An injection catheter comprising:
a catheter body having a longitudinal axis and comprising a flexible tubing having proximal and distal ends and at least one lumen therethrough, the distal end having a distal face;
a needle control handle at the proximal end of the catheter body;
an injection needle extending through the catheter body and needle control handle and having a proximal end attached to the needle control handle and a distal end within the distal end of the catheter body, wherein the injection needle is longitudinally slidable within the catheter body so that upon suitable manipulation of the needle control handle the distal end can extend distally out the distal face of the catheter body in a direction along the longitudinal axis of the catheter body;
an electrode lead wire having a first end electrically connected to the injection needle and a second end electrically connected to a suitable monitoring apparatus or to a source of ablation energy; and
a penetration monitoring electrode fixedly mounted on the injection needle and electrically isolated from the injection needle.

22. An injection catheter according to claim 21, wherein the first end of the electrode lead wire is connected near the proximal end of the injection needle.

23. An injection catheter according to claim 21, wherein the first end of the electrode lead wire is connected near the distal end of the injection needle.

24. An injection catheter according to claim 23, wherein the electrode lead wire comprises a pair of wires including a copper wire and a constantan wire that can act as a thermocouple.

25. An injection catheter according to claim 21, further comprising a protective tube in surrounding relation to at least a portion of the injection needle.

26. An injection catheter according to claim 25, wherein the protective tube surrounds the injection needle along substantially the entire length of the needle.

27. A method for ablating heart tissue comprising:
introducing into a heart of a patient the distal end of a catheter as recited in claim 1;
extending the distal end of the needle electrode distally beyond the distal end of the tip section into the heart tissue;
determining penetration of the needle electrode by using the penetration monitoring electrode fixedly mounted on the injection needle; and
ablating the heart tissue with the needle electrode before, during or after introduction of a fluid.

28. A method according to claim 27, wherein the heart tissue is ablated during introduction of the fluid.

29. A method for ablating heart tissue comprising:
introducing into a heart of a patient the distal end of a catheter as recited in claim 9;
extending the distal end of the needle electrode distally out the distal face of the tip section into the heart tissue;
determining penetration of the needle electrode by using the penetration monitoring electrode fixedly mounted on the injection needle;
introducing a fluid through the needle electrode into the heart tissue; and
ablating the heart tissue with the needle electrode before, during or after introduction of the fluid.

30. The method according to claim 29, wherein the heart tissue is ablated during introduction of the fluid.

31. A method for ablating heart tissue comprising:
introducing into a heart of a patient the distal end of a catheter as recited in claim 21;
extending the distal end of the needle electrode distally out the distal face of the catheter body into the heart tissue;
determining penetration of the needle electrode by using the penetration monitoring electrode fixedly mounted on the injection needle;
introducing a fluid through the needle electrode into the heart tissue; and
ablating the heart tissue with the needle electrode before, during or after introduction of the fluid.

32. The method according to claim 31, wherein the heart tissue is ablated during introduction of the fluid.

33. A method for introducing a therapeutic or diagnostic agent into heart tissue of a patient comprising:
introducing the distal end of a catheter according to claim 21 into the patient's heart;
extending the injection needle distally out the distal face of the catheter body;
determining whether the injection needle has penetrated the heart tissue by using the penetration monitoring electrode fixedly mounted on the injection needle; and
injecting a therapeutic or diagnostic agent into the heart tissue with the injection needle.

34. A method according to claim 33, wherein the determining step comprises measuring the impedance across the electrode mounted on the injection needle.

35. A method according to claim 33, wherein the catheter further comprises at least one additional electrode at or near the distal end of the catheter body.

36. A method according to claim 35, wherein the determining step comprises comparing the impedance across the electrode mounted on the injection needle to the impedance across the additional electrode.

37. The catheter according to claim 1, wherein at least a portion of the injection needle comprises plastic tubing.

38. The catheter according to claim 9, wherein at least a portion of the injection needle comprises plastic tubing.

39. The catheter according to claim 21, wherein at least a portion of the injection needle comprises plastic tubing.

* * * * *